United States Patent
Marin et al.

(10) Patent No.: US 12,290,583 B2
(45) Date of Patent: May 6, 2025

(54) PERFUMING COMPLEX, PERFUMING COMPOSITION AND PERFUMED AQUEOUS COMPOSITION OF NATURAL ORIGIN

(71) Applicant: EXPRESSIONS PARFUMÉES, Grasse (FR)

(72) Inventors: Christophe Marin, Nice (FR); Jennifer Buzzi, Grasse (FR); Juliette Sery, Antibes (FR)

(73) Assignee: EXPRESSIONS PARFUMÉES, Grasse (FR)

( * ) Notice: Subject to any disclaimer, the term of this patent is extended or adjusted under 35 U.S.C. 154(b) by 0 days.

(21) Appl. No.: 18/703,622

(22) PCT Filed: Oct. 21, 2022

(86) PCT No.: PCT/EP2022/079455
§ 371 (c)(1),
(2) Date: Apr. 22, 2024

(87) PCT Pub. No.: WO2023/067179
PCT Pub. Date: Apr. 27, 2023

(65) Prior Publication Data
US 2024/0415745 A1    Dec. 19, 2024

(30) Foreign Application Priority Data

Oct. 22, 2021 (FR) ...................... 2111249

(51) Int. Cl.
| | |
|---|---|
| *A61K 8/06* | (2006.01) |
| *A61Q 13/00* | (2006.01) |
| *C11D 3/00* | (2006.01) |
| *C11D 3/50* | (2006.01) |
| *C11D 17/00* | (2006.01) |

(52) U.S. Cl.
CPC .............. *A61K 8/068* (2013.01); *A61Q 13/00* (2013.01); *C11D 3/0068* (2013.01); *C11D 3/50* (2013.01); *C11D 17/0017* (2013.01); *A61K 2800/262* (2013.01); *A61K 2800/31* (2013.01); *A61K 2800/805* (2013.01)

(58) Field of Classification Search
CPC .... A01N 2300/00; A01N 31/02; A01N 31/08; A01N 31/14
See application file for complete search history.

(56) References Cited

U.S. PATENT DOCUMENTS 7,854,940 B2 * 12/2010 Ciccognani ............ A01N 31/14
424/404

FOREIGN PATENT DOCUMENTS

| CN | 106691896 5 | 5/2017 | |
|---|---|---|---|
| CN | 106691896 A | 5/2017 | |
| EP | 1543829 A1 | 6/2005 | |
| EP | 1543830 A1 | 6/2005 | |
| EP | 2316408 A | 5/2011 | |
| EP | 2316408 A1 | 5/2011 | |
| WO | 9512379 6 | 5/1995 | |
| WO | WO-9512379 A1 * | 5/1995 | ............ A61K 8/068 |
| WO | WO-2005123028 A1 * | 12/2005 | ............ A61K 8/068 |
| WO | 2019154892 A1 | 8/2019 | |

OTHER PUBLICATIONS

International Search Report issued in corresponding International Application No. PCT/EP2022/079455, mailed Feb. 23, 2023, European Patent Office, Rijswijk, Netherlands, pp. 1-3.
Written Opinion issued in corresponding International Application No. PCT/EP2022/079455, mailed Feb. 23, 2023, European Patent Office, Rijswijk, Netherlands, pp. 1-4.

* cited by examiner

*Primary Examiner* — Audrea B Coniglio
(74) *Attorney, Agent, or Firm* — HAUPTMAN HAM, LLP

(57) ABSTRACT

A fragrancing complex comprising: 5% to 70% of a fragrance, IO % to 30% of caprylyl glycol, 0 to 85% of monopropylene glycol, the percentages being expressed by weight relative to the total weight of the 3 components above. The invention relates to a fragrancing composition including: from 25% to 34% of the fragrancing complex described above, from 66% to 75% of a mixture of Polyglyceryl-6 Caprylate/Caprate and Sodium Caproyl/Lauroyl Lactylate, the percentages being expressed by weight relative to the total weight of the 2 components above. A fragranced aqueous composition includes: from 20% to 30% of the fragrancing composition described above, from 70% to 80% of water, the percentages being expressed by weight relative to the total weight of the 2 components above. An embodiment is used in the field of fine perfumery, cosmetics, hygiene products, detergent products and room fragrances or indoor deodorizers or air fresheners.

20 Claims, No Drawings

PERFUMING COMPLEX, PERFUMING COMPOSITION AND PERFUMED AQUEOUS COMPOSITION OF NATURAL ORIGIN

The present application is a U.S. National Phase of International Application Number PCT/EP2022/079455, filed Oct. 21, 2022, which claims priority to French Application No. 2111249, filed Oct. 22, 2021.

TECHNICAL FIELD

The present invention relates to the field of perfumes and perfumed compositions. It finds a particularly advantageous application in the field of fine perfumery, cosmetics, hygiene products to be rinsed or not, ambient fragrances or interior deodorisers, detergents or air fresheners.

PRIOR ART

In the field of perfumery, one recurrent problem relates to the solubility of the perfumes in water. To ensure both solubility and olfactory performance sufficient for the user, it has proved necessary to add certain additives. Such additives have in particular the drawback of leaving a sticky and greasy feel and for the most part irritating the skin. They also modify the properties of the solution that contains them, such as the viscosity and the proportion of foam formed.

Numerous compositions currently marketed contain ethanol. However, ethanol is a VOC (Volatile Organic Compound) that is detrimental with respect to certain regulatory and environmental constraints. In parallel, research made it possible to demonstrate that the presence of water and a reduction or even absence of ethanol made it possible to increase the long-lastingness of the perfume over time, to avoid irritation and drying of the skin and hair, to be free from risks related to exposure to the sun and to avoid any problems related to storage, transport (Customs) and flammability.

In order to remedy the aforementioned drawbacks, compositions based on co-solvents such as isosorbide, solketal and ethers thereof have been proposed. Compositions comprising ethoxylated oleyl alcohol (marketed under the name Ameroscol®) or sulphates, such as sodium lauryl sulfate and sodium laureth sulfate, as surfactants, have also been proposed. However, such compounds are irritating and drying for the skin and hair and are therefore to be avoided in the field of perfumery and cosmetics.

One solution identified by the applicant is described in the patent application WO 2019/154892 A1. This solution consists of a composition comprising solvents selected to ensure a high proportion of perfume without the drawbacks mentioned above. However, consumer demand is more and more turned towards compositions of natural origin. The perfumed compositions offered must however make it possible to solubilise essential oils, which are components that are very difficult to solubilise in water. In addition, the weak performance of solvents and stabilisers of natural origin greatly limit the proportion of perfume possible.

Moreover, this also poses the problem of the transparency of the compositions for facilitating in particular use thereof in various fields without constituting a limitation.

In perfumery, obtaining a fragrant mixture that is both versatile in terms of applications and transparent and which has improved sensory properties and is preferentially stable and of natural origin, is the subject of continuous research.

There is therefore a need to offer a perfumed composition that solves all or some of these drawbacks.

SUMMARY OF THE INVENTION

To achieve this objective, according to one aspect, the invention relates to a perfuming composition comprising the following components:
  from 25 to 34% perfuming complex as described below,
  from 66 to 75% a mixture of polyglyceryl-6 caprylate/caprate and sodium caproyl/lauroyl lactylate,
the percentages being expressed by weight with respect to the total weight of the above 2 components.

The perfuming complex comprising the following components:
  5 to 70% a perfume,
  10 to 30% caprylyl glycol as a solvent, and
  0 to 85% monopropylene glycol as a solvent,
the percentages being expressed by weight with respect to the total weight of the above 3 components.

This perfuming complex has the advantage of allowing solvation of a perfume in a high proportion in solvents of so-called natural origin that are not normally used for this purpose in these proportions. In particular, caprylyl glycol is usually known as an optimiser of preservatives used for protection against microorganisms. To this end, it is used in small quantities and use thereof in the proportions of the present complex does not result from an obvious step in that a minimal quantity is rather sought for an optimum effect for this type of product.

Advantageously, the perfuming complex does not comprise water.

The perfuming complex according to the invention has the advantage of not containing water, which facilitates transport and packaging thereof while being stable and non-irritant for the skin.

The perfuming composition has the advantage of using a solubiliser, also known by the name Easytens S2, which is of natural origin and has a solubilisation synergy with the solvents of the perfume and in particular with monopropylene glycol.

Advantageously, the perfuming composition does not contain water. What is meant by that is that the perfuming composition does not containing added water in addition to the components of said composition. As with the perfuming complex, this facilitates transport and packaging thereof while being stable and non-irritant for the skin.

To achieve this objective, according another aspect, the invention relates to an aqueous perfumed composition comprising the following components:
  from 20 to 30% the perfuming composition as described above,
  from 70 to 80% water,
the percentages being expressed by weight with respect to the total weight of the above 2 components.

Advantageously, the perfumed aqueous composition is in the form of microemulsion.

According to another aspect, the invention relates to a method for preparing a perfuming composition as described above:
  preparing a perfuming complex as described above,
  heating the mixture of polyglyceryl-6 caprylate/caprate and sodium caproyl/lauroyl lactylate, preferentially at a maximum of 65° C.,
  adding the heated mixture of polyglyceryl-6 caprylate/caprate and sodium caproyl/lauroyl lactylate to the perfuming complex, homogenising the perfuming composition obtained.

According to another aspect, the invention relates to a method for preparing an aqueous perfumed composition as described above:
- adding water to the perfuming composition described above, and
- homogenising the aqueous perfumed composition obtained.

The invention also relates to a cosmetic base, a detergent base or an ambient fragrance comprising the perfumed aqueous composition or the perfuming composition or the perfuming complex as described above.

The invention also relates to the use of the perfumed aqueous composition, of the cosmetic base or of the detergent base or of the ambient fragrance as described above for masking bad smells. Preferentially, the perfuming complex, the perfuming composition and the aqueous perfumed composition are of natural origin, even more preferentially COSMOS certifiable.

Finally, the formula produced is compatible, whatever the perfume and the olfactory family selected.

DETAILED DESCRIPTION

Before giving a detailed review of embodiments of the invention, optional features are set out below, which can optionally be used as an alternative to or in combination with one another.

According to one example, the perfumed aqueous composition or the perfuming composition or the perfuming complex is transparent.

According to one example, the perfumed aqueous composition is in the form of microemulsion.

According to one example, the perfumed aqueous composition or the perfuming composition or the perfuming complex does not comprise any ethoxylated solvent.

According to one example, the method for preparing the perfumed aqueous composition comprises a subsequent step of adding a preservative, for example in a quantity of between 0.8% and 1.2%, preferably in a quantity less than or equal to 1% by weight of the total weight of the composition. Preferentially, the method comprises mixing as far as homogenisation. This preservative is an additive. As is normal, the additives and in particular the preservatives are counted in the quantity of water. Preferentially, the quantity of water described comprises water and any additives, in particular of the preservative type.

According to one example, the method for preparing the perfumed aqueous composition comprises a subsequent step of maceration, chilling, preferentially at 4°, and then filtration.

According to another aspect, the invention relates to the use of the perfumed aqueous composition or the perfuming composition or the perfuming complex as described above for fine perfumery.

According to another aspect, the invention relates to the use of the perfumed aqueous composition or the perfuming composition or the perfuming complex as described above for cosmetics.

According to another aspect, the invention relates to the use of the perfumed aqueous composition or the perfuming composition or the perfuming complex as described above for hygiene products intended to be rinsed, such as shower gels, shampoo etc, or not, such as deodorants etc.

According to another aspect, the invention relates to the use of the perfumed aqueous composition or the perfuming composition or the perfuming complex as described above for ambient fragrances or interior deodorisers or air fresheners or detergent products.

"Compatible with any type of olfactory family" means that said composition can contain any type of perfume, of any olfactory family.

"High proportion of perfume" means that the perfumed aqueous composition can contain up to 10% by weight perfuming complex.

"Stable" means a composition that does not degrade over time and the compounds of which will not react with each other. "Stable" means that the homogeneity, the colouring, the olfactory intensity, the olfactory quality and the viscosity of the composition are preserved. More particularly, the composition according to the present invention is stable under accelerated ageing after 24 hr under UV (Suntest) and after 2 months at 25° C. and 45° C. in comparison with a sample that remained at 5° C., away from light.

"Without ethanol" or "without isopropanol" means a composition containing 0% by weight ethyl alcohol or 0% by weight isopropyl alcohol.

"Without ethoxylated compound" means a composition containing 0% by weight ethoxylated compounds, i.e. ones containing the —(—CH2-CH2-O—) unit.

"Transparent" means that said composition is transparent at temperatures between 4 and 50° C. whatever the perfume used. Transparent composition means a composition the turbidity of which is below 12 NTU (Nephelometric Turbidity Unit), preferably below 7 NTU. This preferentially being measured by means of a turbidity meter of the HI88713 ISO Turbidity Meter type of the Hanna Instruments brands.

"Pleasant smell" means a smell that is detected by the olfactory sense of the human being and is perceived as being pleasant.

"Having a viscosity close to that of water" means that the dynamic viscosity of said composition at 20° C. is between 1 and 50 mPa·s, preferentially between 1 and 40 mPa·s, preferentially between 1 and 30 mPa·s, preferentially between 1 and 10 mPa·s. According to the present invention, the dynamic viscosity is measured with the Viscotester IQ viscometer, geometry CC27 DG/TI—01160025, at 20° C., at 500 s−1 for 30 seconds.

"Perfume" means a composition comprising a mixture of perfuming substances, said perfuming substances being in the isolated state, in solution or in suspension, in their normal diluents, dissolvers or co-ingredients. Such a composition is intended to provide a pleasant olfactory component.

"Perfuming substance" means one or more raw perfumed materials of natural or synthetic origin "Perfumed aqueous composition" means a composition comprising more than 50% water and a perfume or a perfuming complex or a perfuming composition.

COSMOS certifiable means that the complex, the perfuming composition and/or the perfumed aqueous composition meets the criteria for obtaining the COSMOS label in force in 2022.

The percentages mean mass percentage, i.e. by weight with respect to a weight of the complex or of a composition.

Cosmetic base means adult, child, baby or animal toilet waters, body mist, hairspray, sun-protection water, solutions for towelettes etc.

Detergent base means a perfume for laundry, a perfume for detergent, a perfume for the floor, etc.

Ambient fragrance means a perfumed composition for the house, car, closed public, work, private or environmental spaces, fabrics, etc.

According to a first aspect, the present invention relates to a perfuming complex comprising a perfume, a first solvent and a second solvent.

The perfuming complex advantageously comprises a perfume in a quantity of between 5 and 70% by weight of the total weight of the perfuming complex, preferentially from 5 to 55%, preferentially 5 to 50%. The total weight of the perfuming complex means the sum of a perfume, of the first solvent and of the second solvent.

The perfuming complex advantageously comprises a first solvent in a quantity of between 0 and 85% by weight of the total weight of the perfuming complex, preferentially from 35 to 85%.

Preferentially, the first solvent is monopropylene glycol the CAS number of which is 57-55-6.

Monopropylene glycol is a COSMOS-certified hydrophilic plant-based solvent used in perfumery. The chemical formula thereof is as follows:

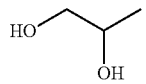

Its log P of −0.92 gives it a hydrophilic character particularly advantageous for formulating an aqueous microemulsion. Nevertheless, it is this hydrophilic character that makes it an ineffective perfumery solvent.

The perfuming complex advantageously comprises a second solvent in a quantity of between 10 and 30% by weight of the total weight of the perfuming complex, optionally from 10 to 20%, or even from 10 to 15%.

Preferentially, the second solvent is caprylyl glycol. Caprylyl glycol is known by the CAS number 1117-86-8. Caprylyl glycol is also known by the name A-Leen 8 or 1,2-Octanediol. The chemical formula thereof is as follows:

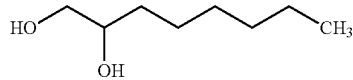

Surprisingly, the applicant has identified solvent properties of this raw material known for its properties of improving the properties of preservatives. Caprylyl glycol makes it possible to prepare a homogeneous and transparent perfumed composition.

Advantageously, the perfuming complex does not comprise water.

According to one embodiment, the perfuming complex is intended to be used in a perfuming composition preferentially not containing added water, or a perfumed aqueous composition, i.e. mixed with water.

Advantageously, the perfuming complex consists of 5 to 70% perfume, 0 to 85% monopropylene glycol and 10 to 30% caprylyl glycol by weight of the total weight of the perfuming complex.

According to a second aspect, the present invention relates to a perfuming complex comprising the perfuming complex described above and a solubiliser.

Preferentially, the perfuming complex comprises the perfuming complex in a quantity of between 25 and 34% by weight of the total weight of the perfuming composition. The total weight of the perfuming composition means the sum of the perfuming complex and of the solubiliser.

Preferentially, the perfuming composition comprises the solubiliser in a quantity greater than or equal to 66%, preferentially between 66 and 75% by weight of the total weight of the perfuming composition. According to a preferred embodiment, the solubiliser is a mixture of polyglyceryl-6 caprylate/caprate (and) sodium caproyl/lauroyl lactylate also known by the name Easytens S2 marketed by Lavollee and produced by Hydrior.

This solubiliser is a mixture of COSMOS surfactants. The solubilising properties of the molecules contained in this mixture were studied to obtain synergy. This solubiliser makes it possible to obtain very satisfactory results in cutting with perfume. Moreover, surprisingly, this solubiliser operates in synergy with the solvents selected for the perfuming complex, which makes it possible to obtain a transparent homogeneous solution in water. This raw material is suitable as a solubilising agent in a COSMOS microemulsion. Advantageously, the perfuming composition is configured not to foam excessively, or have excessively high viscosity, which are parameters that make it difficult to use the perfuming composition during manufacture and/or the manufacture of the perfumed aqueous composition.

Preferentially, the perfuming composition does not comprise added water. The perfuming composition does not contain water as a component in addition to the other components of the perfuming composition.

Preferentially, the perfuming composition consists of 25 to 34% perfuming complex by weight of the total weight of the perfuming composition and at least 66%, preferentially from 66 to 75%, the mixture of polyglyceryl-6 caprylate/caprate (and) sodium caproyl/lauroyl lactylate, by weight of the total weight of the perfuming composition.

The perfuming composition thus comprises:
from 1.25 to 23.8% perfume,
from 0 to 28.9% monopropylene glycol,
from 2.5 to 10.2% caprylyl glycol,
from 66 to 75% a mixture of polyglyceryl-6 caprylate/caprate (and) sodium caproyl/lauroyl lactylate.

According to a third aspect, the invention relates to a perfumed aqueous composition comprising the perfuming composition cited above and water.

Advantageously, the perfumed aqueous composition comprises from 20 to 30% the perfuming composition described above. Preferentially, the perfumed aqueous composition comprises the remaining quantity of water, preferentially from 70 to 80% water. The percentages are by weight of the total weight of the perfumed aqueous composition. Preferentially, the quantity of water includes any additives such as preservatives.

Advantageously, the perfumed aqueous composition comprises:
from 5 to 10% the perfuming complex described above,
from 13.2 to 22.5% solubiliser, i.e. the mixture of polyglyceryl-6 caprylate/caprate (and) sodium caproyl/lauroyl lactylate described above, preferentially at least 13.2%,
and a complementary quantity of water to make up 100%, i.e. conventionally of the order of 70 to 80%.

The percentages are by weight of the total weight of the perfumed aqueous composition.

The perfumed aqueous composition thus comprises:
from 0.25 to 7.14% perfume,
from 0 to 8.67% monopropylene glycol,
from 0.5 to 3.06% caprylyl glycol, from 13.2 to 22.5% mixture of polyglyceryl-6 caprylate/caprate (and) sodium caproyl/lauroyl lactylate, preferentially at least 13.2%, from 70 to 80% water, According to one embodiment, the perfumed aqueous composition comprises a preservative. Preferentially, the preservative is present in a quantity of between 0.8 and 1.2%, preferentially less than or equal to 1%. Advantageously, the quantity of preservative is provided in the total quantity of water.

Advantageously, the perfumed aqueous composition and/or the perfuming composition is transparent.

Advantageously, the perfumed aqueous composition is a microemulsion.

The perfumed aqueous composition is said to be aqueous since the composition comprises a majority of water. Advantageously, the perfumed aqueous composition is an oil-in-water microemulsion.

Advantageously, the perfumed aqueous composition and/or the perfuming composition does not comprise ethoxylated solvent.

Advantageously, the perfumed aqueous composition and/or the perfuming composition does not contain paraben.

Advantageously, the perfumed aqueous composition and/or the perfuming composition does not contain sulfate.

Advantageously, the perfumed aqueous composition has a viscosity similar to water. The texture is thus light.

Advantageously, the perfumed aqueous composition is sprayable.

Advantageously, the perfumed aqueous composition and/or the perfuming composition does not dry the skin and thus has emollient properties.

Advantageously, the perfumed aqueous composition foams little.

Advantageously, the perfumed aqueous composition and/or the perfuming composition is of natural origin.

Advantageously, the perfumed aqueous composition and/or the perfuming composition is COSMOS certifiable.

According to another aspect, the invention relates to a method for preparing the perfumed aqueous composition.

The method comprises the preparation of the perfuming complex. The preparation of the perfuming complex comprises mixing the perfume with the first solvent and the second solvent.

The method next comprises preparing the perfuming composition. This step comprises a heating of the mixture of polyglyceryl-6 caprylate/caprate (and) sodium caproyl/lauroyl lactylate. The heating is implemented by means known to a person skilled in the art, such as for example convection heating by storing in a hot chamber, or conduction heating (bain marie, sand bath, hotplate, double jacket, etc). The heating is implemented until a viscosity allowing ease of use is obtained. Advantageously, the heating is implemented at a maximum temperature of 65° C.

The step of preparing the perfuming composition comprises, after the heating step, a step of mixing the heated mixture of polyglyceryl-6 caprylate/caprate (and) sodium caproyl/lauroyl lactylate with the perfuming complex. The mixing is implemented until a homogeneous and transparent perfuming composition is obtained, advantageously without a volute.

The method next comprises preparing the perfumed aqueous composition from the perfuming composition obtained previously. The perfuming composition is mixed with water. The mixing is implemented until a homogeneous and transparent perfumed aqueous composition is obtained, advantageously without a volute.

According to one embodiment, the method comprises a step of adding a preservative to the perfumed aqueous composition.

According to one example, the method for manufacturing the perfumed aqueous composition optionally comprises a maceration step, preferentially of 2 to 4 weeks, then a chilling step, preferentially at 4°, and a filtration step. This step is implemented after the water and preservatives are added.

The aqueous perfumed composition is able to be packaged in many types of packaging suitable for receiving an aqueous liquid composition. By way of non-limitative example, tubes, bottles, sprays, vaporisers, roll-ons, pots, brushes with reservoir, pencils with reservoir, etc.

The perfume according to the invention can comprise ingredients preferentially of natural origin, optionally synthetic. The choice of this perfume depends firstly on the odorising effect sought and secondly the application in which it will be incorporated.

Such raw materials, whether they be of natural or synthetic origin, can comprise esters, ethers, alcohols, aldehydes, ketones, lactones, acetals, nitriles, phenols, acids, terpenes, heterocyclic nitrogen or sulphur compounds, saturated or unsaturated, and complex products of natural origin. Examples of esters comprise, but are not limited to, benzyl acetate, p-tert-butylcyclohexyl acetate, 3,7-dimethyl-1,6-octadien-3-yl acetate (linalyl acetate), dimethyl-benzyl-carbinyl acetate, phenylethyl acetate, 1,1-dimethyl-2-phenylethyl acetate, linalyl benzoate, ethyl-methyl-phenyl glycinate, allylcyclohexyl propionate, styralyl propionate, benzyl salicylate, methyl-3-oxo-2-pentylcyclopentane acetate, prop-2-enyl-2,3-methylbutoxy acetate (allyl amyl glycolate, 3-methylbutoxy-acetic acid, 2-propenyl ester), acetic acid phenylmethyl ester, isoamyl acetate (isopentyl acetate), cis-hex-3-nyl acetate ((Z)-hex-3-enyl acetate), citronellyl acetate (3,7-dimethyl-6-octen-1-ol acetate), hexyl acetate, isobornyl acetate (bicyclo[2.2.1]heptan-2-ol, 1,7,7-trimethyl exo-acetate), methanyl acetate, (alpha,alpha,4-trimethylcyclohexylmethyl acetate), ethyl acetate, prenyl acetate (3-methyl-2-butenyl acetate), triethyl citrate, 4-ter-Butylcyclohexyl acetate, (3R-(3alpha,3abeta,6alpha,7beta,8aalpha))-Octahydro-3,6,8,8-tetramethyl-1H-3a-7-methanoazulene-5-yl acetate, 3,7-Dimethyl octa-1,6-diene-3-yl acetate, 1,4-Dioxacyclohexadecane-5,16-Dione, benzyl 2-hydroxybenzoate, (Z)-3-Hexenyl-2-hydroxybenzoate, 2-(1,1 (dimethylethyl) Cyclohexyl acetate, isopentyl acetate, methyl phenylacetate, (Z)-Hex-3-enyl acetate, 3,7-Dimethyl octa-1,6-diene-3-yl acetate, 3-Methyl-2-butenyl acetate, alpha-Methyl-Benzenemethanol acetate, methyl 2-aminobenzoate, 2-Propenyl-(cyclohexyloxy) acetate, methyl 2,4-dihydroxy-3,6-dimethylbenzoate, methyl 3-oxo-2-pentylcyclopentaneacetate, 3-alpha, 4,5,6,7,7-alpha-Hexahydro-4,7-methano-1H-inden-6-yl propanoate, methyl 3-oxo-2-pentylcyclopentaneacetate, 2-(1,1-Dimethylethyl) Cyclohexyl acetate, hexyl-2-hydroxybenzoate, (benzoic acid 2-hydroxy-2-hexyl ester), 3a,4,5,6,7,7a-Hexahydro-4,7-methanoinden-6-yl acetate, ethyl 2-methylbutyrate 3a,4,5,6,7,7a-Hexahydro-4,7-methano-1H-inden-5-yl, 2-methylpropanoate, alpha, alpha-Dimethylphenethyl acetate, 3,7-Dimethyl octa-1,6-diene-3-yl acetate, d'exo-1,7,7-trimethyl-bicyclo[2.2.1]heptan-2-ol acetate, ethyl hexanoate, 3,7-Dimethyl octa-1,6-diene-3-yl acetate, methyl 3-oxo-2-pentylcyclopentaneacetate, Methyl 2-(methylamino) benzoate, 10-Undecenoic acid, ethyl ester, ethyl 2-methylpentanoate, cis-3,7-Dimethyl-2,6-octadienyl ethanoate, benzyl 2-hydroxybenzoate, (Z)-Hex-3-enyl acetate, benzoic acid 2-hydroxy-2-hexyl ester, prop-2-enyl-2-cyclohexyloxyacetate (2-Propenyl-(cyclohexyloxy) acetate), acetic acid (3-Methylbutoxy), 2-Propenyl ester, 2-Phenyl ethanol, hexyl acetate, (1R, 2S, 5R)-5-Methyl-2-(1-methylethyl)-cyclohexanol ethanoate, terpenyl acetate (4-methyl-1-propan-2-yl-1-cyclohex-2-enyl acetate), alpha-3,3-trimethylcyclohexyl-methyl formiate, 3-methylbutyl butanoate (iso amyl butyrate), alpha, alpha-dimethylphenethyl butanoate, 3-dihydrodicyclopentadien-2,3-yl acetate, prop-2-enyl 3-cyclohexyl propanoate (allyl cyclohexane propionate), allyl heptanoate (2-propenyl heptanoate), 2-phenoxy-ethyl 2-methylpropanoate (phenoxy ethyl isobutyrate), ethyl 2-methylpentanoate, ethyl 2-methyl-butyrate (2-methyl-butanoic acid ethyl ester), 1,4 dioxacycloheptadecane-5,17-dione (ethylene brassylate), (2S)-2-propyl-1,1-dimethylpropoxy propionate, ((2S)-2-(1,1-dimethylpropoxy)-propanoic acid propyl ester), 2-tert-butylcyclohexyl acetate (2-(1,1-dimethylethyl) cyclohexyl acetate), ci-3-hexenyl salicylate, [(1S)-3-(4-methylpent-3-enyl)-1-cyclohex-3-enyl]methyl acetate, 3-pentyltetrahydro[2H]pyranyl acetate, linalyl propionate, cetyl acetate, cedryl acetate, anisyl acetate, nopyl acetate, neryl acetate, 3a,4,5,6,7,7a-hexahydro-4,7-methanoinden-6-yl acetate, 3a,4,5,6,7,7a-hexahydro-4,7-methano-1H-inden-6-yl propanoate, 2-propenyl 3-cyclohexanepropanoate, 1,2,3-triethyl 2-hydroxypropane-1,2,3-tricarboxylate, (2E)-3,7-dimethylocta-2,6-dien-1-yle acetate, 3,5,5-trimethylhexyl acetate, 3,7-dimethyl-octa-1,6-diene-3-yl acetate, cis-3,7-dimethyl-2,6-octadienyl ethanoate, tetradecanoic acid 1-methylethyl ester, 2-hydroxy-benzoic acid 3-methylbutylic ester, 2-hydroxy-benzoic acid phenylmethyl ester, 2-hydroxy-benzoic acid 2-hexyl ester, 2-hydroxy-benzoic acid methyl ester, acetoacetique acid ethyl ester, 3,7-dimethyl-octa-1,6-diene-3-yl acetate, 1,2-benzenedicarboxylic acid 1,2-diethyl ester, (Z)-hex-3-enyl 2-methylpropanoate, (4-methyl-1-propan-2-yl-1-cyclohex-2-enyl) acetate, 3a,4,5,6,7,7a-hexahydro-4,7-methanoinden-6-yl acetate, ethyl 2,3-epoxy-3-phenylbutyrate, methyl 2-aminobenzoate, methyl 2-(methylamino) benzoate, methyl benzoate, methyl 2,4-dihydroxy-3,6-dimethylbenzoate, (3R-(3alpha,3beta,6beta, 7beta, 8alpha))-octahydro-6-methoxy-3,6,8,8-tetramethyl-1H-3a,7-methanoazulene acetate, hexyl salicylate, 4-tert-butylcyclohexyl) acetate, methyl palmitate, 1,6-octadiene-3-ol, 3,7-dimethyl-acetate and triethyl citrate. Preferably, examples of esters comprise linalyl propionate, cetyl acetate, cedryl acetate, anisyl acetate, nopyl acetate, neryl acetate, hexyl acetate (3R-(3alpha,3beta, 6beta,7beta,8alpha))-octahydro-6-methoxy-3,6,8,8-tetramethyl-1H-3a, 7-methanoazulene, hexyl salicylate, 4-tert-butylcyclohexyl) acetate, methyl palmitate, 1,6-Octadien-3-ol, 3,7-dimethyl-acetate, linalyl acetate and triethyl citrate.

Examples of ethers comprise, but are not limited to, benzyl ether, ethyl ether, ambergris, diphenyl oxide, 4,6,6,7,8,8-hexamethyl-1,3,4,6,7,8-hexahydrocyclopenta[g]isochromene, amber carane, 1,1-dimethoxy-2,2,5-trimethyl-4-hexene, 3,4,4a,5,8,8a-Hexahydro-3',7'-dimethylspiro(1,4-methanonaphthalene-2 (1H),2'-oxirane), 2,4,6-Trimethyl-4-phenyl-1,3-dioxane, Benzene, 1,1'-Oxybis, Methyl 2-naphthyl ether, ethyl 2-naphthyl ether, 2,4-Dimethyl-4-phenyltetrahydrofuran, (ethoxymethoxy)cyclododecane, (E)-1-methoxy-4-(1-propenyl)-benzene, 1-methoxy-4-(2-propenyl)-benzene, methyl cedryl ether and 2-naphtyl ethyl ether. Preferably, examples of ethers comprise 1,1-dimethoxy-2,2,5-trimethyl-4-hexene, methyl cedryl ether and 2-naphtyl ethyl ether.

Examples of alcohols comprise, but are not limited to, menthol ([1R-(1alpha,2beta, 5alpha)]-5-methyl-2-isopropylcyclohexanol), citronellol, geraniol, linalool (for example ethyl linalool and tetrahydrolinalool), phenylethyl alcohol, terpineol, 2,6-dimethylheptan-2-ol, 2-methyl-1-phenylpropan-2-ol (dimethyl phenyl carbinol), 3-methyl-5-[2,2,3-trimethylcyclopent-3-en-1-yl]pent-4-en-2-ol, 2-phenylethanol, 2-ethyl-4-(2,2,3-trimethyl-1-cyclopent-3-enyl) but-2-en-1-ol, (E)-4-methyldec-3-en-5-ol, cinnamic alcohol (3-phenyl-2-propen-1-ol), 3,7-Dimethyl-6-octen-1-ol, p-menth-1-en-8-ol, cis-Hex-3-en-1-ol, 4-Methyl-3-decen-5-ol, 2,6-dimethyloct-7-en-2-ol, 1,1'-Oxydipropan-2-ol, 3,7-Dimethyl-1,6-nonadien-3-ol, 1,1'-Oxydipropan-2-ol, 2,6-dimethyloct-7-en-2-ol 3,7-Dimethyl octa-1,6-diene-3-ol, 2-ethyl-4-(2,2,3-trimethyl-3-cyclopenten-1-yl)-2-buten-1-ol, phenylmethanol, 4-Methyl-3-decen-5-ol, 2,6-Dimethyl-octan-2-ol, 3,7-Dimethyl-6-octen-1-ol, 4-(1,1-dimethylethyl)-Cyclohexanol, (2E)-3,7-dimethyl-2,6-Octadien-1-ol, Hexan-1-ol, exo-1,7,7-Trimethylbicyclo[2.2.1]heptan-2-ol, 2-(2,2,7,7-tetramethyltricyclo[6.2.1.0 (1,6)]undec-5 (4)-en-5-yl) propan-1-ol, 1-Phenylethanol, 1,1'-Oxydipropan-2-ol, 3,7-Dimethyloctan-3-ol, cis-3,7-Dimethyl-2,6-octadien-1-ol, 3,7-Dimethyl-6-octen-1-ol, Hex-2-en-1-ol, 3,7-Dimethyl octa-1,6-diene-3-ol, 2-Methyl-4-phenylbutan-2-ol, 2,6-Octadien-1-ol, 3,7-dimethyl-, (2E)-, p-menth-1-en-8-ol, 3-Phenylpropan-1-ol, phenylmethanol, 2,6-dimethyloct-7-en-2-ol, alpha,beta,2,2,3-pentamethylcyclopent-3-ene-1-butanol, 3-(5,5,6-trimethylbicyclo[2.2.1]hept-2-yl) cyclohexan-1-ol (IBCH), cis-3-hexen-1-ol, methyl-trimethylbicyclo-hexylmethyl-cyclopropyl methanol benzyl alcohol, endo-1,7,7-trimethyl-bicyclo-[2.2.1]heptan-2-ol, 3,7-dimethyl-6-octen-1-ol, 3,7-dimethyl-1-octanol, (2E)-3,7-dimethyl-2,6-octadien-1-ol, cis-3,7-dimethyl-2,6-octadien-1-ol, 3,7-dimethyl-octa-1,6-diene-3-ol, 2-(4-methyl-1-cyclohex-3-enyl) propan-2-ol, 4-methyl-1-(1-methylethyl)-3-cyclohexen-1-ol, (1R, 2S, 5R)-5-methyl-2-(1-methylethyl)-cyclohexanol, (2E)-3,7-dimethyl-2,6-octadien-1-ol and 3-methylbutan-1-ol. Preferably, examples of alcohols comprise alpha, beta,2,2,3-pentamethylcyclopent-3-ene-1-butanol, 3-(5,5,6-trimethylbicyclo[2.2.1]hept-2-yl) cyclohexan-1-ol (IBCH), cis-3-hexenol, methyl-trimethylbicyclohexylmethyl-cyclopropyl methanol, 3-methylbutan-1-ol, ethyl linalool, tetrahydrolinaool and [1R-(1alpha,2beta, 5alpha)]-5-methyl-2-isopropylcyclohexanol (menthol).

Examples of aldehydes comprise, but are not limited to, linear alkanals comprising between 8 and 18 carbon atoms, 3,7-Dimethyl-2,6-octadienal (citral), citronellal, Cyclamen aldehyde, hydroxycitronellal, 3,7-Dimethyl-2,6-octadienal, Undecanal, alpha-methyl-4-(1-methylethyl)-Benzenepropanal, 3-(4-isopropylphenyl)-2-methylpropanal, 2,4-dimethyl-cyclohex-3-ene-1-carbaldehyde, 2,4-dimethylcyclohex-3-ene-1-carbaldehyde, (2E)-2-Dodecenal, Octanal, Lauryl aldehyde, Nonanal, (E)-2-Benzylideneoctanal, 2,4-dimethylcyclohex-3-ene-1-carbaldehyde, 3-(4-ethylphenyl)-2,2-dimethylpropanal, 4-Hydroxy-3-methoxybenzaldehyde, 3-(4-tert-butylphenyl)-2-methylpropanal, 3-(4-tert-butylphenyl) propanal, 2,6,10-trimethylundec-9-enal, 4 (octahydro-4,7-methano[5H]inden-5-ylidene) butanal, 3-(3-propan-2-ylphenyl) butanal, 7-hydroxy-3,7-dimethyloctanal (hydroxycitronellal, 3,7-dimethyl-7-hydroxy-octane-1-al), 4-(4-hydroxy-4-methylpentyl)cyclohex-3-ene-1-carbaldehyde, octahydro-5-methoxy-4,7-methano-1H-indene-2-carboxaldehyde, alpha-methyl cinnamic aldehyde (2-methyl-3-phenyl-2-propenal), 4-methoxybenzaldehyde (anisic aldehyde), C10 aldehyde (decanal), undec-10-enal, C12 aldehyde (lauric or dodecanal), methyl-nonyl acetaldehyde (2-methylundecanal), C16 aldehyde, C6 aldehyde (hexanal), cinnamic aldehyde (3-phenyl-2-propenal), 3-ethyoxy-4-hydroxybenzaldehyde (Ethylvanillin), hexyl cinnamic aldehyde (2-benzylideneheptanal), 3-phenylbutanal (3-phenylbutyraldehyde), 2,4-dimethylcyclohex-3-ene-1-carbaldehyde, 5-heptanal, 2,6-dimethylhept-5-enal, 4-hydroxy-3-methoxybenzaldehyde (Vanillin), alpha-methyl-1,3-benzodioxole-5-propionaldehyde, 4-isopropyl-benzaldehyde, 3,7-dimethyl-6-octenal, 3,7-dimethyl-2,6-octadienal, 4-(4-hydroxy-4-methylpentyl)-3-cyclohexene-1-carboxaldehyde, trans-hex-2-enal, 2,4,6-trimethyl-3-cyclohexene-1-carboxaldehyde, 2-(4-tert-butylbenzyl)propionaldehyde and benzaldehyde. Preferably, examples of aldehydes comprise 2,4-dimethylcyclohex-3-ene-1-carbaldehyde, 5-heptanal, 2,6-dimethyl-hept-5-enal, 4-hydroxy-3-methoxybenzaldehyde (Vanillin), alpha-methyl-1,3-benzodioxole-5-propionaldehyde, citral and benzaldehyde.

Examples of ketones comprise, but are not limited to, ionones, isomethylionone, methyl cedryl, (E)-1-(2,6,6-trimethyl-1-cyclohex-2-enyl) but-2-en-1-one (alpha-damascone), 3-methyl-2-[(2Z)-pent-2-en-1-yl]cyclopent-2-en-1-one (cis-jasmone), 4-(4-methoxyphenyl)-butan-2-one, 4 (3)-(4-methylpent-3-enyl)cyclohex-3-enecarbaldehyde, 1-(1,2,3,4,5,6,7,8-octahydro-2,3,8,8-tetramethyl-2-naphthalenyl) ethanone, 3-Methyl-4-(2,6,6-trimethyl-2-cyclohexenyl)-3-buten-2-one, (E)-4-(2,6,6-trimethyl-1-cyclohexen-1-yl)-3-buten-2-one, E)-4-(2,6,6-trimethylcyclohex-2-eneyl)-but-3-en-2-one, 7-Methyl-2H-benzo-1,5-dioxepin-3 (4H)-one, 1-(2,6,6-Trimethyl-1,3-cyclohexadienyl)-2-buten-1-one, Methyl hydroxypyrone, 2,2,5-Trimethyl-5-pentylcyclopentan-1-one, 1-(5,5-Dimethyl-1-cyclohexenyl) pent-4-en-1-one, 3-Methyl-4-(2,6,6-trimethyl-2-cyclohexenyl)-3-buten-2-one, 2-[2-(4-Methyl-3-cyclohexen-1-yl) propyl]-cyclopentanone, 1-(1,2,3,4,5,6,7,8-octahydro-2,3,8,8-tetramethyl-2-naphthalenyl) ethanone, (E)-4-(2,6,6-trimethyl-1-cyclohexen-1-yl)-3-buten-2-one, 4-Phenylbutan-2-one 2-Cyclohexyl-1,6-heptadien-3-one, 1-(5,5-Dimethyl-1-cyclohexenyl) pent-4-en-1-one, 2-Buten-1-one, 1-(2,6,6-trimethyl-3-cyclohexen-1-yl)-, 2H-1-Benzopyran-2-one, 1-spiro(4.5)-7-decen-7-yl-4-penten-1-one and 1-spiro(4.5)-6-decen-7-yl-4-penten-1-one, (E) 1-(2,6,6-Trimethyl-2-cyclohexen-1-yl)-2-buten-1-one, (E)-4-(2,6,6-trimethyl-1-cyclohexen-1-yl)-3-buten-2-one, Dihydro-5-pentyl-2 (3H)-furanone, 2,2,5-Trimethyl-5-pentylcyclopentan-1-one, 1-(1,2,3,4,5,6,7,8-octahydro-2,3,8,8-tetramethyl-2-naphthalenyl) ethanone, methyl 7-cedryl ketone, methylbenzo[b][1,4]dioxepin-3-one, 1,7,7-trimethylbicyclo[2,2,1]heptan-2-one, 1-benzopyrane-2-one (Coumarine), 1-(2,6,6-trimethyl-1-cyclohex-3-enyl) but-2-en-1-one, butan-2,3-dione (Diacetyl), 1-(1,2,3,4,5,6,7,8-octahydro-2,3,8,8,-tetramethyl-2-naphthyl) ethan-1-one, irones, 1-(2-naphthalenyl) ethanone (2-acetonaphtone), menthone, carvone, 3-methyl-2-pentyl-2-cyclopentenone, 1-(2,6,6-trimethyl-3-cyclohexen-1-yl)-2-buten-1-one, 1-(2,6,6-trimethyl-2-cyclohexenyl) hepta-1,6-dien-3-one, 2-ethyl-3-hydroxy-4H-pyran-4-one, (5R)-2-methyl-5-prop-1-en-2-ylcyclohex-2-en-1-one, 1-(6-tert-butyl-1,1-dimethyl-2,3-dihydro-1H-inden-4-yl) ethanone, 1-(5,6,7,8-tetrahydro-3,5,5,6,8,8-hexamethyl-2-naphthyl) ethan-1-one, 4-(2,6,6-trimethylcyclohex-2-enyl)-but-3-ene-2-one, octan-2-one, 1-(1,2,3,4,5,6,7,8-Octahydro-2,3,8,8-Tetramethyl-2-Napthyl) Ethan-1-one and 1,3,4,6,7,8a-Hexahydro-1,1,5,5-tetramethyl-2H-2,4a-methanonaphthalen-8 (5H)-one. Preferably, examples of ketones comprise irones, 1-(2-naphthalenyl) ethanone (2-acetonaphtone), menthone, carvone, 3-methyl-2-pentyl-2-cyclopentenone, 1-(1,2,3,4,5,6,7,8-Octahydro-2,3,8,8-Tetramethyl-2-Napthyl) Ethan-1-one and 1,3,4,6,7,8a-Hexahydro-1,1,5,5-tetramethyl-2H-2,4a-methanonaphthalen-8 (5H)-one.

Examples of lactones comprise, but are not limited to, gamma decalactone (decan-4-olide), Decan-5-olide, Decan-4-olide, Undecan-4-olide gamma undecalactone (undecan-4-olide), cis-jasmone lactone, gamma undecalactone, delta octalacone, delta decalactone and hexahydro-3,6-dimethyl-2 (3H)-benzofuranone. Preferably, examples of lactones comprise gamma undecalactone, delta octalacone, delta decalactone and hexahydro-3,6-dimethyl-2 (3H)-benzofuranone.

Examples of acetals comprise, but are not limited to, 2,4-dimethyl tetrahydroindenodioxine, aldehyde phenylacetic diacetal, phenylacetaldehyde glycerylacetal, citral diethyl acetal, citral dimethyl acetal, 2,6-octadienal, 1,1-dimethoxy-2-phenylethane and 3,7-dimethyl isomerise acid. Preferably, examples of acetals comprise phenylacetaldehyde glycerylacetal, citral diethyl acetal, citral dimethyl acetal, 2,6-octadienal and 3,7-dimethyl isomerise acid.

Examples of nitriles comprise, but are not limited to, 3,7-dimethyloct-6-ene nitrile (citronellyl nitrile), tridec-2-enenitrile, 3-phenyl-2-propenenitrile, 3,7-Dimethyl-6-enenitrile, dodecanenitrile and 3,7-dimethylnona-2,6-dienenitrile. Preferably, examples of nitriles comprise tridec-2-enenitrile, 3-phenyl-2-propenenitrile, dodecanenitrile and 3,7-dimethylnona-2,6-dienenitrile.

Examples of phenols comprise, but are not limited to, eugenol (2-methoxy-4-(2-propenyl)-phenol), iso-eugenol, 5-methyl-2-(1-methylethyl)-phenol, 2-ethoxy-4-methylphenol, 2-isopropyl-5-methylphenol, 5-methyl-2-(1-methylethyl)-Phenol, 2,6-di-tert-butyl-p-cresol and 2-ethoxy-4-(methoxymethyl)-phenol.

Examples of acids comprise, but are not limited to, pentanoate acid, butyric acid and 2-methylpent-2-en-1-oic acid.

Examples of terpenes such as cyclic terpene hydrocarbons (for example sesquiterpenic) or non-cyclic, comprise, but are not limited to, limonene, 1-methyl-4-isopropenyl-1-cyclohexene, 1-methyl-4-isopropyl-1,4-cyclohexadiene, 7-methyl-3-methyleneocta-1,6-diene, 1-methyl-4-(1-methylethyl)-1,3-cyclohexadiene, 2,6,6-trimethylbicyclo[3.1.1]hept-2-ene, 6,6-dimethyl-2-methylenebicyclo[3.1.1]heptane, 2,2-dimethyl-3-methylenebicyclo-[2.2.1]-heptane, (3R-(3alpha,3abeta, 6beta, 7beta,8aalpha))-Octahydro-6-methoxy-3,6,8,8-tetramethyl-1H-3a,7-methanoazulene, 4,11,11-trimethyl-8-methylene-(1R,4E,9S)-Bicyclo[7.2.0.]undec-4-ene, [1R, (1R*,4E,9S*)]-4,11,11-trimethyl-8-methylene-bicyclo[7.2.0]undec-4-ene, 1-methyl-4-(1-methylethyl)benzene and sesquiterpene essential oils. Preferably, examples of terpenes comprise sesquiterpene essential oils.

Examples of heterocyclic nitrogen or sulphur compounds, saturated or unsaturated, comprise, but are not limited to, indole, 1,3-benzopyrrole, tetrahydro-4-methyl-2-(2-methyl-1-propenyl)-2H-pyrane, 2-methyl-pyrazine, 4-methyl-5-hydroxyethyl thiazole (2-(4-methylthiazol-5-yl) ethanol), 6-tert-butylquinoline, 6-(isopropyl) quinoline, (3aR-(3aalpha,5abeta,9aalpha,9bbeta))-Dodecahydro-3a,6,6,9a-tetramethylnaphtho (2,1-b) furan, 2-Isopropyl-4-methyl-1,3-thiazole, cis-2-methyl-4-propyl-1,3-oxathiane, 6 (8)-(1-Methylpropyl) Quinoleine and pyrazines. Preferably, examples of heterocyclic nitrogen or sulphur compounds, saturated or unsaturated, comprise 6-tert-butylquinoline, 6-(isopropyl) quinoline, cis-2-methyl-4-propyl-1,3-oxathiane, 6 (8)-(1-Methylpropyl)Quinolene and pyrazines.

Examples of complex products of natural origin comprise, but are not limited to, essential oils extracted from various parts of plants (flowers, stems, leaves, fruits, peels, roots, woody parts, herbs, needles, sap and gums), resinoids, and concretes or absolutes obtained therefrom. Preferably, examples of complex products of natural origin comprise *Artemisia herba-alba* oil, *Pogostemon cablin* leaf oil, *Citrus nobilis* peel oil, *Barosma betulina* leaf extract, *Citrus limon* peel extract, *Eucalyptus globulus* leaf oil, *Dipterocarpus turbinatus* balsam oil, *Pogostemon cablin* leaf oil, *Rosmarinus officinalis* leaf oil, *Juniperus virginiana* oil, *Mentha arvensis* leaf oil, *Mentha viridis* leaf oil, *Citrus Aurantium dulcis* peel oil, *Citrus Aurantium dulcis* peel extract, *Cupressus sempervirens* leaf oil, patchouli (*Pogostemon cablin*) leaf oil, Texas cedar (*Juniperus mexicana*) oil and *Lavandula hybrida* oil (*Lavandula Hybrida*).

The perfumed aqueous composition may optionally comprise one or more additional ingredients, selected from solvents, diluents, additives, excipients, etc. The raw materials and the appropriate quantities are well known to a person skilled in the art.

According to a particular embodiment, the perfumed aqueous composition according to the invention further comprises at least one additive selected from antifoaming agents, antioxidants, chelating agents, UV filters, preservatives, thickeners, cosmetic active ingredients, hydrating agents, moisturisers, softeners, pigments, dyes, refrigerants, pH adjusters, bactericides, bacteriostatic agents, insecticides, repellents, glitter, active agents and mixtures thereof. Preferentially, the quantity of water added is deduced from the quantity of these additives so that the sum of the water and any additives lies in the range of the quantity of water described above. The embodiments detailed above can easily be combined with each other non-limitatively.

EXAMPLES

Example 1: Perfume No. 1

The components described in table 1 are mixed in order to obtain perfume No. 1.

| Perfume 1 | |
|---|---|
| Raw materials | Proportions (%) |
| Essential oil (EO) of orange | 60.00 |
| EO of bergamot | 20.00 |
| EO of petitgrain | 10.00 |
| EO of lemon | 4.00 |
| Ethyl citrate | 2.80 |
| EO of mandarin | 2.00 |
| EO of ylang | 1.00 |
| EO of neroli | 0.20 |

Example 2: Perfumed Aqueous Composition No 1

The components described in table 2 are mixed in order to obtain perfumed aqueous composition No 1.

| Perfumed aqueous composition 1 | |
|---|---|
| Raw materials | Proportions (%) |
| Perfume 1 | 5.10 |
| Monopropylene glycol | 3.90 |
| Caprylyl glycol (A-Leen 8) | 1.00 |
| Polyglyceryl-6 caprylate/caprate and sodium caproyl/lauroyl lactylate (Easytens S2). | 20.00 |
| Water | 69.00 |
| Preservative | 1.00 |
| Results at D + 1 | Clear |

The perfumed aqueous composition according to the invention is transparent and homogeneous. Perfumed aqueous composition 1 is formulated from a perfuming complex comprising: 51% perfume No 1, 10% caprylyl glycol and 39% monopropylene glycol. The percentages being expressed by weight with respect to the total weight of the above 3 components. Then 10% of the perfuming complex is mixed with 20% a mixture of polyglyceryl-6 caprylate/caprate and sodium caproyl/lauroyl lactylate, preferentially heated. Finally, 69% water is added to the mixture to obtain perfumed aqueous composition 1. The percentages being expressed by weight with respect to the total weight of the perfumed aqueous composition.

The preservative used is a preservative complying with the COSMOS charter in force in 2022, soluble in water and transparent. The preservative selected is Epsan C.

Example 3: Perfume No. 2

The components described in table 3 are mixed in order to obtain perfume No. 2.

| Perfume 2 | |
|---|---|
| Raw materials | Proportions (%) |
| EO of lemon | 44.94 |
| Terpenes of orange | 33.71 |
| Ethyl citrate | 1.18 |
| Linalyl acetate | 8.43 |
| EO of clary sage | 2.25 |
| Citral | 2.25 |
| EO of cardamom | 1.35 |
| Ethyl caproate 10% sol. ethyl citrate | 1.12 |
| EO of cedar | 1.12 |
| EO of pepper | 0.90 |
| EO of ginger | 0.90 |
| EO of caraway | 0.56 |
| $CO_2$ extract of ginger | 0.45 |
| EO of eucalyptus | 0.34 |
| EO of peppermint | 0.22 |
| Melonal | 0.22 |
| EO of lentisk | 0.06 |

Example 4: Perfumed Aqueous Compositions No 2 to 4

The components described in table 4 are mixed in order to obtain perfumed aqueous compositions No 2 to 4.

| | Perfumed aqueous compositions | | |
|---|---|---|---|
| | 2 | 3 | 4 |
| Raw materials | Proportions (%) | | |
| Perfume 2 | 8.10 | 8.10 | 7.00 |
| Monopropylene glycol | 1.90 | 0.90 | — |
| Caprylyl glycol (A-Leen 8) | — | 1.00 | 3.00 |
| Polyglyceryl-6 caprylate/caprate and sodium caproyl/lauroyl lactylate (Easytens S2). | 20.00 | 20.00 | 20.00 |
| Water | 69.00 | 69.00 | 69.00 |
| Preservative | 1.00 | 1.00 | 1.00 |
| Results at D + 1 | Phase separation | Phase separation | Clear |

Perfumed aqueous compositions 2, 3, 4 are formulated from perfuming complexes comprising: 81% or 70% perfume No 2, 0 or 10% or 30% caprylyl glycol and 0 or 9 or 19% monopropylene glycol. The percentages being expressed by weight with respect to the total weight of the above 3 components. Then 10% of the perfuming complex is mixed with 20% a mixture of polyglyceryl-6 caprylate/ caprate and sodium caproyl/lauroyl lactylate, preferentially heated. Finally, 69% water is added to the mixture to obtain perfumed aqueous compositions 2, 3, 4. The percentages being expressed by weight with respect to the total weight of the perfumed aqueous composition. The preservative used is a preservative complying with the COSMOS charter in force in 2022, soluble in water and transparent. The preservative selected is Epsan C.

It is clear from these various perfumed aqueous compositions that the solvent caprylyl glycol (A-Leen 8) participates in obtaining a transparent homogeneous composition.

Perfumed aqueous composition 4 is produced with the largest quantity of perfume in the perfuming complex, namely 70% by weight of the total weight of the perfuming complex, i.e. 7% by weight of the total weight of the final perfumed aqueous composition number 4.

This perfumed aqueous composition is produced with the largest quantity of A-Leen 8 in the perfuming complex, namely 30% by weight of the total weight of the perfuming complex, i.e. 3% by weight of the total weight of the final perfumed aqueous composition number 4.

This perfumed aqueous composition is produced with the smallest quantity of monopropylene glycol in the perfuming complex, namely 0% by weight of the total weight of the perfuming complex, i.e. 0% by weight of the total weight of the final perfumed aqueous composition number 4.

The perfumed aqueous composition 4 according to the invention is transparent and homogeneous.

Example 5: Perfume No 3

The components described in table 5 are mixed in order to obtain perfume No 3.

| Perfume 3 | |
| --- | --- |
| Raw materials | Proportions (%) |
| Linalool | 16.13 |
| Geraniol | 16.13 |
| Linalyl acetate | 16.13 |
| Citronellol | 11.29 |
| EO of orange | 8.06 |
| EO of lemon | 8.06 |
| Alpha-terpineol | 8.06 |
| EO of mandarin | 1.61 |
| Gamma undecalactone | 1.61 |
| Benzyl salicylate | 1.61 |
| Ethyl citrate | 1.52 |
| Cis-3-hexenyl acetate | 1.29 |
| EO of palmarosa | 1.13 |
| EO of bucchu | 0.97 |
| EO of geranium | 0.97 |
| Gamma decalactone | 0.81 |
| Isoamyl acetate | 0.81 |
| Benzyl acetate | 0.81 |
| Phenylethyl alcohol | 0.81 |
| Beta-ionone | 0.81 |
| Ethyl acetate | 0.48 |
| EO of cardamom | 0.16 |
| Coumarin | 0.16 |
| Raspberry ketone | 0.16 |
| Veltol | 0.16 |
| $CO_2$ extract of blackcurrant | 0.10 |
| Methyl anthranylate | 0.08 |
| Hexanal | 0.08 |

Example 6: Perfumed Aqueous Composition No 5

The components described in table 6 are mixed in order to obtain perfumed aqueous composition No 5.

| Perfumed aqueous composition 5 | |
| --- | --- |
| Raw materials | Proportions (%) |
| Perfume 3 | 0.50 |
| Monopropylene glycol | 8.00 |
| Caprylyl glycol (A-Leen 8) | 1.50 |
| Polyglyceryl-6 caprylate/caprate and sodium caproyl/lauroyl lactylate (Easytens S2). | 20.00 |
| Water | 69.00 |
| Preservative | 1.00 |
| Result at D + 1 | Clear |

Perfumed aqueous composition 5 is formulated from a perfuming complex comprising:

5% perfume No 3, 15% caprylyl glycol and 80% monopropylene glycol. The percentages being expressed by weight with respect to the total weight of the above 3 components. Then 10% of the perfuming complex is mixed with 20% a mixture of polyglyceryl-6 caprylate/caprate and sodium caproyl/lauroyl lactylate, preferentially heated. Finally, 69% water is added to the mixture to obtain perfumed aqueous composition No 5. The percentages being expressed by weight with respect to the total weight of the perfumed aqueous composition. The preservative used is a preservative complying with the COSMOS charter in force in 2022, soluble in water and transparent. The preservative selected is Epsan C.

This perfumed aqueous composition is produced with the smallest quantity of monopropylene glycol in the perfuming complex, namely 5% by weight of the total weight of the perfuming complex, i.e. 0.5% by weight of the total weight of the final perfumed aqueous composition number 5.

The perfumed aqueous composition according to the invention is transparent and homogeneous.

Example 7: Perfume No 4

The components described in table 7 are mixed in order to obtain perfume No 4.

| Perfume 4 | |
| --- | --- |
| Raw materials | Proportions (%) |
| EO of bergamot | 21.71 |
| Linalool | 15.50 |
| Benzyl acetate | 12.40 |
| EO of orange | 9.30 |
| Citronellol | 7.75 |
| Alpha-terpineol | 6.20 |
| EO of mandarin | 6.20 |
| Phenylethyl alcohol | 2.48 |
| EO of palmarosa | 2.48 |
| Indole 10% sol. ethyl citrate | 1.55 |
| Cis-3-hexenyl acetate | 1.55 |
| EO of lavender | 1.55 |
| EO of davana | 1.24 |
| EO of petitgrain | 0.93 |
| Gamma undecalactone | 0.93 |
| Methyl anthranylate | 0.93 |
| EO of cedar | 0.93 |
| Phenylethyl acetate | 0.93 |
| EO of ylang | 0.93 |
| Coumarin 10% sol. ethyl citrate | 0.62 |
| Raspberry ketone | 0.62 |

-continued

| Perfume 4 | |
|---|---|
| Raw materials | Proportions (%) |
| Vanillin | 0.62 |
| EO of neroli 10% sol. ethyl citrate | 0.62 |
| Beta-ionone | 0.31 |
| Cis-3-hexenol | 0.31 |
| Eugenol | 0.31 |
| EO of cardamom | 0.31 |
| Veltol | 0.31 |
| Gamma decalactone | 0.16 |
| Ethyl citrate | 0.16 |
| Acetyl methyl carbinol 10% sol. ethyl citrate | 0.16 |

Example 8: Perfumed Aqueous Composition No 6

The components described in table 8 are mixed in order to obtain perfumed aqueous composition No 6.

| Perfumed aqueous composition 6 | |
|---|---|
| Raw materials | Proportions (%) |
| Perfume 4 | 0.50 |
| Monopropylene glycol | 8.50 |
| Caprylyl glycol (A-Leen 8) | 1.00 |
| Polyglyceryl-6 caprylate/caprate and sodium caproyl/lauroyl lactylate (Easytens S2). | 20.00 |
| Water | 69.00 |
| Preservative | 1.00 |
| Result at D + 1 | Clear |

Perfumed aqueous composition 6 is formulated from a perfuming complex comprising:

5% perfume No 4, 10% caprylyl glycol and 85% monopropylene glycol. The percentages being expressed by weight with respect to the total weight of the above 3 components. Then 10% of the perfuming complex is mixed with 20% a mixture of polyglyceryl-6 caprylate/caprate and sodium caproyl/lauroyl lactylate, preferentially heated. Finally, 69% water is added to the mixture to obtain perfumed aqueous composition 6. The percentages being expressed by weight with respect to the total weight of the perfumed aqueous composition. The preservative used is a preservative complying with the COSMOS charter in force in 2022, soluble in water and transparent. The preservative selected is Epsan C.

This perfumed aqueous composition is produced with the largest quantity of A-Leen 8 in the perfuming complex, namely 10% by weight of the total weight of the perfuming complex, i.e. 1% by weight of the total weight of the final perfumed aqueous composition number 6.

This perfumed aqueous composition is produced with the largest quantity of monopropylene glycol in the perfuming complex, namely 85% by weight of the total weight of the perfuming complex, i.e. 8.5% by weight of the total weight of the final perfumed aqueous composition number 6.

The perfumed aqueous composition according to the invention is transparent and homogeneous.

Example 9: Perfumed Aqueous Composition No 7

The components described in table 9 are mixed in order to obtain perfumed aqueous composition No 7.

| Perfumed aqueous composition 7 | |
|---|---|
| Raw materials | Proportions (%) |
| Perfume 1 | 7.10 |
| Monopropylene glycol | 3.70 |
| Caprylyl glycol (A-Leen 8) | 1.20 |
| Polyglyceryl-6 caprylate/caprate and sodium caproyl/lauroyl lactylate (Easytens S2). | 18.00 |
| Water | 69.00 |
| Preservative | 1.00 |
| Result at D + 1 | Turbidity |

Perfumed aqueous composition 7 is formulated from a perfuming complex comprising:

59.17% perfume No 1, 10% caprylyl glycol and 30.83% monopropylene glycol. Then 12% perfuming complex is mixed with 18% a mixture of polyglyceryl-6 caprylate/caprate and sodium caproyl/lauroyl lactylate, preferentially heated. Finally, 69% water is added to the mixture to obtain perfumed aqueous composition 7.

The preservative used is a preservative complying with the COSMOS charter in force in 2022, soluble in water and transparent. The preservative selected is Epsan C.

This perfumed aqueous composition is produced with a quantity of Easytens S2 solubiliser less than our selection, i.e. 18% by weight of the total weight of the final perfumed aqueous composition number 7.

The perfumed aqueous composition is not transparent.

Example 10: Perfumed Aqueous Composition No 8

The components described in table 10 are mixed in order to obtain perfumed aqueous composition No 8.

| Perfumed aqueous composition 8 | |
|---|---|
| Raw materials | Proportions (%) |
| Perfume 1 | 7.10 |
| Monopropylene glycol | 2.90 |
| Caprylyl glycol (A-Leen 8) | 2.00 |
| Polyglyceryl-6 caprylate/caprate and sodium caproyl/lauroyl lactylate (Easytens S2). | 18.00 |
| Water | 69.00 |
| Preservative | 1.00 |
| Result at D + 1 | Turbidity |

Perfumed aqueous composition 8 is formulated from a perfuming complex comprising: 59.17% perfume No 1, 16.67% caprylyl glycol and 24.16% monopropylene glycol. Then 12% perfuming complex is mixed with 18% a mixture of polyglyceryl-6 caprylate/caprate and sodium caproyl/lauroyl lactylate, preferentially heated. Finally, 69% water is added to the mixture to obtain perfumed aqueous composition 8.

The preservative used is a preservative complying with the COSMOS charter in force in 2022, soluble in water and transparent. The preservative selected is Epsan C.

This perfumed aqueous composition is produced with a quantity of Easytens S2 solubiliser less than our selection, i.e. 18% by weight of the total weight of the final perfumed aqueous composition number 8.

The perfumed aqueous composition is not transparent.

The invention is not limited to the aforementioned embodiments, and includes all the embodiments and uses covered by the application.

The invention claimed is:

1. A perfuming composition comprising the following components:
   between 25 and 34% a perfuming complex comprising the following components: between 5 and 70% a perfume, between 10 and 30% caprylyl glycol as a solvent, between 0 and 85% monopropylene glycol as solvent, the percentages being expressed by weight with respect to the total weight of the above 3 components, and
   between 66 and 75% a mixture of polyglyceryl-6 caprylate/caprate and sodium caproyl/lauroyl lactylate,
   the percentages being expressed by weight with respect to the total weight of the above 2 components.

2. The perfuming composition according to claim 1, wherein the perfuming complex is free of water.

3. A perfuming aqueous composition comprising the following components:
   between 20 to 30% the perfuming composition according to claim 1, and
   between 70 to 80% water,
   the percentages being expressed by weight with respect to the total weight of the above 2 components.

4. The perfuming aqueous composition according to claim 3, wherein the perfuming aqueous composition is in the form of microemulsion.

5. The perfuming aqueous composition according to claim 3, wherein the perfuming aqueous composition is transparent.

6. The perfuming aqueous composition according to claim 3, wherein the perfuming aqueous composition is free of an ethoxylated solvent.

7. The perfuming aqueous composition according to claim 3, wherein the perfuming aqueous composition is of natural origin.

8. A method for preparing a perfuming composition according to claim 1, comprising:
   preparing the perfuming complex,
   heating the mixture of polyglyceryl-6 caprylate/caprate and sodium caproyl/lauroyl lactylate,
   adding the heated mixture of polyglyceryl-6 caprylate/caprate and sodium caproyl/lauroyl lactylate to the perfuming complex, and
   homogenising the perfuming composition obtained.

9. A method for preparing a perfumed aqueous composition according to claim 3, comprising:
   adding water to a perfuming composition, wherein the perfuming composition comprises the following components:
      between 25 and 34% a perfuming complex comprising the following components: between 5 and 70% a perfume, between 10 and 30% caprylyl glycol as a solvent, between 0 and 85% monopropylene glycol as solvent, the percentages being expressed by weight with respect to the total weight of the above 3 components, and
      between 66 and 75% a mixture of polyglyceryl-6 caprylate/caprate and sodium caproyl/lauroyl lactylate, the percentages being expressed by weight with respect to the total weight of the above 2 components, and
   homogenising the perfumed aqueous composition obtained.

10. The method for preparing according to claim 9, comprising a subsequent step of adding a preservative.

11. The method for preparing according to claim 9, comprising a subsequent maceration step, an icing step, and a filtration step.

12. A method of using the perfuming aqueous composition according to claim 3, comprising applying the perfuming aqueous composition as all or part of a cosmetic base or of a fine perfumery product or of a detergent base or of an ambient fragrance.

13. A cosmetic base, a detergent base or an ambient fragrance comprising the perfumed aqueous composition according to claim 3.

14. The method according to claim 12, wherein applying the perfuming aqueous composition comprises masking bad smells.

15. The method for preparing according to claim 9, comprising a subsequent step of adding a preservative in a quantity of between 0.8% and 1.2%, by weight of a total weight of the composition.

16. A method of using the perfuming composition according to claim 1, comprising applying the perfuming composition as all or part of a cosmetic base or of a fine perfumery product or of a detergent base or of an ambient fragrance.

17. A cosmetic base, a detergent base or an ambient fragrance comprising the perfuming composition according to claim 1.

18. The perfuming composition according to claim 1, wherein the perfuming composition is transparent.

19. The perfuming composition according to claim 1, wherein the perfuming composition is free of an ethoxylated solvent.

20. The perfuming composition according to claim 1, wherein the perfuming composition is of natural origin.

* * * * *